US007097612B2

(12) United States Patent
Bertolero et al.

(10) Patent No.: US 7,097,612 B2
(45) Date of Patent: Aug. 29, 2006

(54) TISSUE POSITIONER

(75) Inventors: Arthur A. Bertolero, Danville, CA (US); Tamer Ibrahim, Oakland, CA (US)

(73) Assignee: Endoscopic Technologies, Inc.

( * ) Notice: Subject to any disclaimer, the term of this patent is extended or adjusted under 35 U.S.C. 154(b) by 181 days.

(21) Appl. No.: 10/903,732

(22) Filed: Jul. 29, 2004

(65) Prior Publication Data

US 2005/0033110 A1 Feb. 10, 2005

Related U.S. Application Data

(60) Provisional application No. 60/491,323, filed on Jul. 29, 2003, provisional application No. 60/519,837, filed on Nov. 11, 2003.

(51) Int. Cl.
*A61F 13/00* (2006.01)

(52) U.S. Cl. ............... 600/37; 600/201; 600/228; 600/231

(58) Field of Classification Search .............. 600/37, 600/201, 206, 208, 227–228, 230–231; 601/132; 602/4.6, 60–61, 75–76, 903; 606/151; 128/897–898
See application file for complete search history.

(56) References Cited

U.S. PATENT DOCUMENTS

| 6,899,670 B1* | 5/2005 | Peng et al. ................ 600/37 |
| 2005/0222528 A1* | 10/2005 | Weston ........................ 602/1 |
| 2005/0222544 A1* | 10/2005 | Weston ...................... 604/313 |

* cited by examiner

*Primary Examiner*—John P. Lacyk
(74) *Attorney, Agent, or Firm*—GSS Law Group; Gregory Scott Smith

(57) ABSTRACT

Apparatus and methods for stabilizing and/or positioning tissues or organs during surgical procedures. One feature of the positioners of the invention includes the use of one or more suction elements used to grip the organ or tissue. The main body of the suction element comprises body defining a polyhedral shaped chamber, an elliptical ring structure and a vacuum port. The invention further includes structures to support the suction element and hold the suction element and attached tissue in a fixed position including catheters, lockable flexible arms, and retractors.

69 Claims, 8 Drawing Sheets

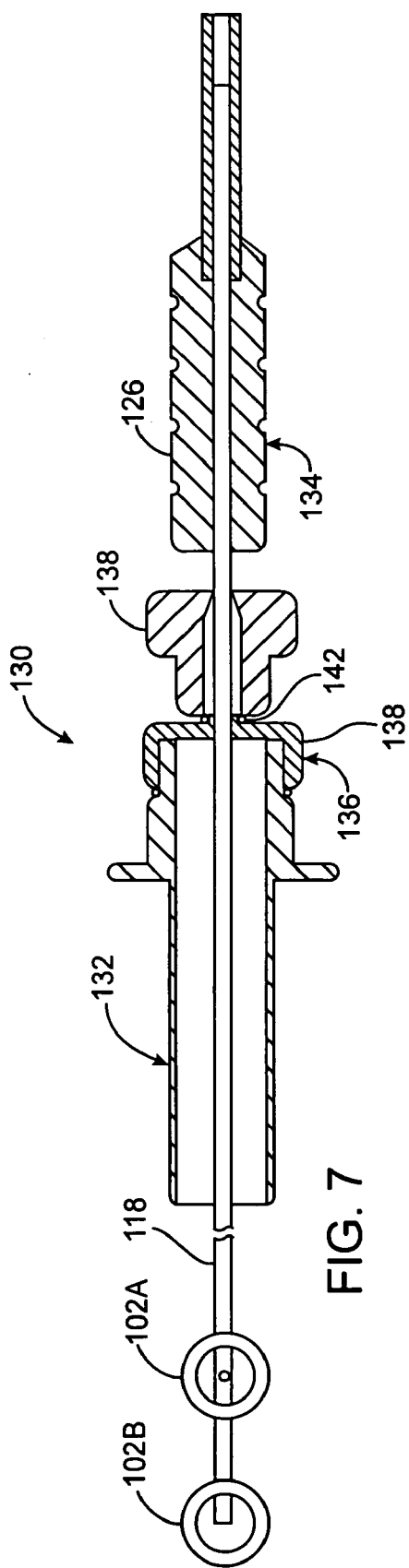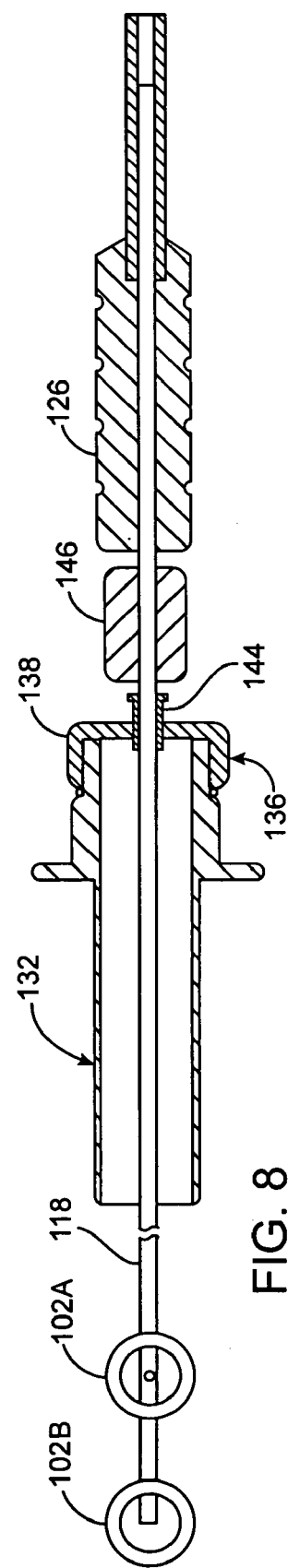

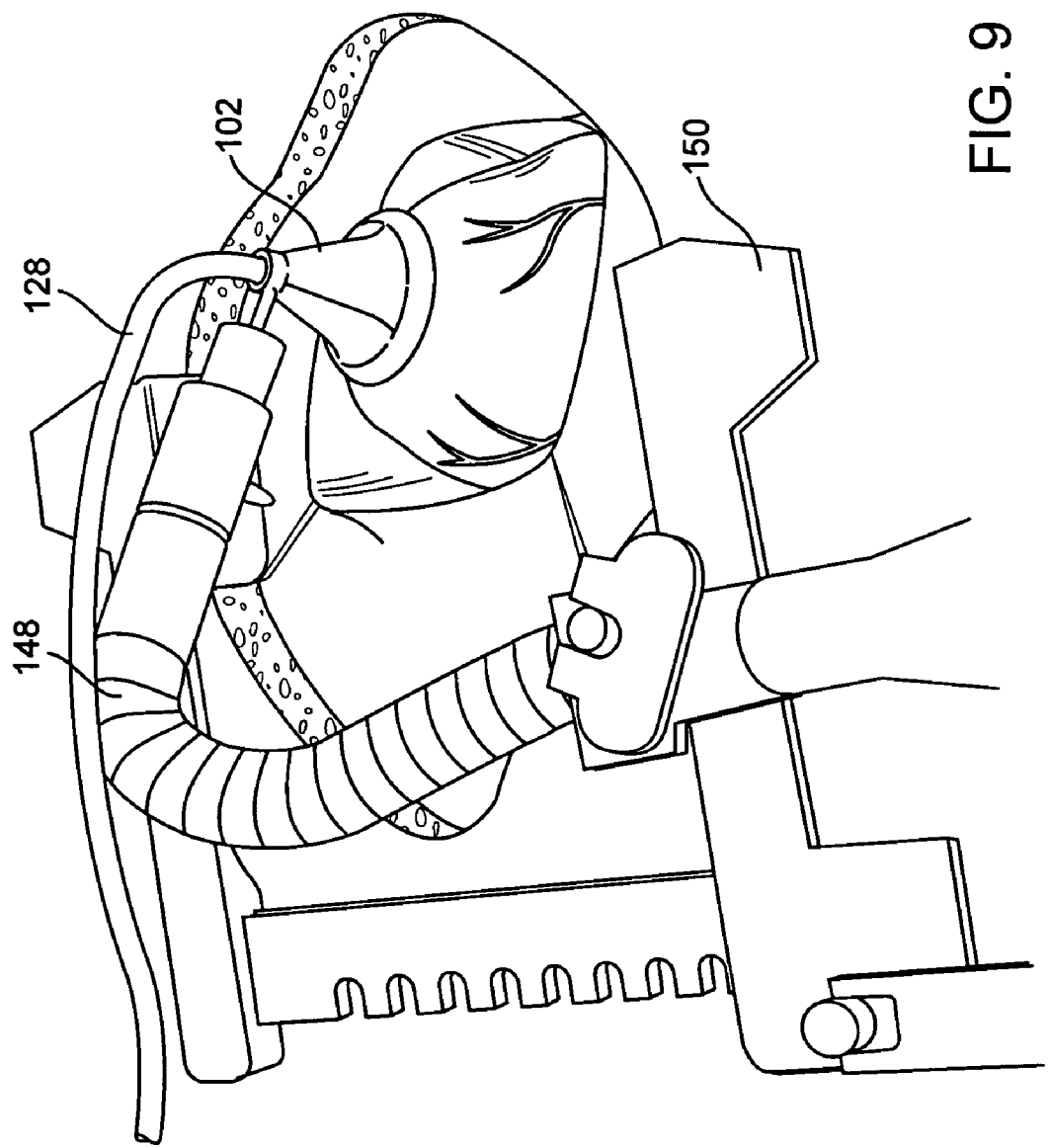

TISSUE POSITIONER

CROSS REFERENCE TO RELATED APPLICATIONS

This application claims priority of U.S. provisional patent application Ser. No. 60/491,323, filed Jul. 29, 2003, and of U.S. provisional patent application Ser. No. 60/519,837, filed Nov. 11, 2003, and are hereby incorporated by reference in their entirety.

FIELD OF THE INVENTION

The invention pertains to devices and methods for stabilizing and positioning organs and tissues and to methods for using such devices.

BACKGROUND OF THE INVENTION

Internal organs often need to be positioned and/or stabilized for specific surgical medical procedures. In some procedures, the surgeon may wish to move or orient the organ so that surgery may be performed upon it more easily. In other cases, the surgeon may wish to hold the organ, or a portion of it, immobile so that the organ will not move during the surgical procedure so that the area that is being operated on is stable to ensure the accuracy of the surgeon's work. In still other cases, the surgeon may simply want to move the organ out of the way to improve access or visualization. There is a desire in the art to avoid having the use of a tissue positioner cause damage to the tissue that is being grasped. This is particularly important when operating on an internal organ such as the heart. What is needed is a tissue positioner that can be used in both open surgical procedures and through small incisions and ports, that has a small profile thereby increasing the overall visibility of the surgeon, and which may include multiple suction or contact points to limit the gross tissue damage per area by distributing vacuum force over multiple attachments.

SUMMARY OF THE INVENTION

The invention includes a device and method to facilitate manipulation and positioning of tissues and organs during surgery. One feature of the positioners of the invention includes the use of one or more suction elements used to grip the tissue or organ to be positioned. Tissues positioners built in accord with the invention are particularly suited for use on the heart during in both open and closed chest surgical procedures and in both stopped and beating heart surgical procedures.

Some embodiments of the invention include a positioner for manipulating the heart that includes a vacuum tube communicating with at least one suction element. In some embodiments the suction elements includes a polyhderal-shaped vacuum chamber, a vacuum port in gas communication with the chamber, and an elliptical shaped ring at an opening of the chamber for contacting the surface of the tissues to be positioned. In some embodiments the polyhedral shape includes acute angles between adjacent side walls of the chamber. In some embodiments, the elliptical ring is preferably circular, and can be located just outside or just inside the opening of the vacuum chamber. In some embodiments the elliptical ring includes a midline whereby tissue may be drawn through the elliptical ring above the midline of the elliptical ring to enhance the grip of the suction element on the tissues to be positioned. In some embodiments the suction element further includes a screen or mesh divider that may prevent tissue from being drawn too far into the chamber, and may, in effect, divide the chamber into two. The chamber of the suction element is generally defined by three or more side walls, and in some embodiments preferably four side walls. In some embodiments, one or more of the walls may include a texture on an interior surface the walls to assist in gripping the tissue drawn into the suction element.

In some embodiments the suction element is fabricated from a medical grade flexible polymeric material, which may allow the suction element to flex when attached to a beating heart to reduce impairment of heart function caused by using the suction element to position the heart. In some embodiments it is preferred that the ratio of the area of the opening of the vacuum port and the area of the opening of the vacuum chamber is approximately 1:4.

In embodiments for use in minimally invasive procedures, the size of the suction elements may be selected to facilitate introduction through a 5 to 30 mm port. However, in other embodiments, the selected sizes could be different. In some embodiments the suction elements are replaceable. In some embodiments, a means for holding one or more suction element of the invention, including but not limited to lockable flexible arms, retractors, catheters, vacuum tubes, rods, cannula, and fixed arms, may be introduced to a surgical field, and then one or more suction elements are affixed to the holding means through another opening in the surgical field.

The invention may also include any of a variety of kinds of vacuum sources. The tissue positioner is configured so that vacuum is communicated to each suction element, and the tissue positioner may be constructed so that vacuum is communicated to each suction element in series, or constructed so that vacuum is communicated in parallel. The suction elements are designed to attach to tissue and maintain a seal under vacuum to accumulate negative pressure. Once attached, the suction element may be manipulated by the user to move or adjust the tissue to which it is adhered. The invention may also include apparatus for holding the suction element in a fixed position, in order to hold the tissue grabbed by the suction element in a fixed selected position. Many kinds of holding apparatus are useable including, but not limited to: lockable flexible arms, retractors, catheters, vacuum tubes, rods, cannula, and fixed arms.

In some embodiments, more than two suction elements may be used. The suction elements may be supported a fixed distance apart. In some embodiments the material between the suction elements may be malleable or steerable allowing the suction elements to be moved in a desired orientation and position relative to each other and to the tissue to be positioned.

The invention also includes method of using the positioner of the invention. One such method includes the steps of providing a positioner in accord with the invention, introducing the suction elements of the positioner into a patient, attaching at least one suction element to tissue under vacuum, and manipulating the positioner to position the tissue in a fixed position. For embodiments including more than one suction element, the method can also include the steps: attaching a first suction element to tissue via vacuum, then manipulating the positioner to conform to a topography of the tissue to be positioned and attaching a second suction element to the tissue via vacuum.

BRIEF DESCRIPTION OF THE DRAWINGS

FIG. 7 shows a cutaway side view of positioner of the invention extending through a cannula.

FIG. 8 shows a side view of another combination positioner and cannula assembly in accord with the invention.

FIG. 9 shows a positioner of the invention including a single suction element grasping a heart, with the positioner coupled to a retractor by a lockable flexible arm.

DETAILED DESCRIPTION

The invention pertains to apparatus and methods for stabilizing and/or positioning tissues or organs during surgical procedures and to methods for using such apparatus. One aspect of the invention comprises a positioner particularly suited for positioning the heart during surgical procedures on or near the heart in animals and humans. The positioner can be used in closed chest or open chest surgical procedures, and when used in surgical procedures performed on the heart, in both beating heart or stopped heart surgical procedures. Positioning the heart may include pushing or rolling the heart in addition to lifting the heart or otherwise manipulating the heart. The positioner allows a surgeon to improve patient care and to perform surgery in a controlled fashion with reproducibly good results.

One feature of the positioners of the invention includes the use of one or more suction elements used to grip the heart, or other organ or tissue. The suction elements are configured to provide a good seal with, and effective grip on, the surface of the tissue on which they are suctioned. Each suction element includes a main body with a selected geometry and a sealing means at the base of the body that interfaces with tissue. In some embodiments, the main body of the suction element is polygonal tetrahedron shaped, or somewhat pyramid shape. The tissue positioner is configured so that vacuum is communicated to each suction element. The tissue positioner maybe constructed so that vacuum may be communicated to each suction element in series or constructed so that vacuum is communicated in parallel. The suction elements are designed to attach to tissue and maintain a seal under vacuum to accumulate negative pressure. Once attached, the apparatus supporting the suction elements may be manipulated by the user to move or adjust the tissue to which the suction elements are adhered. Example embodiments will be discussed with reference to the figures with like numbers referring to similar parts and feature.

Figure 1:
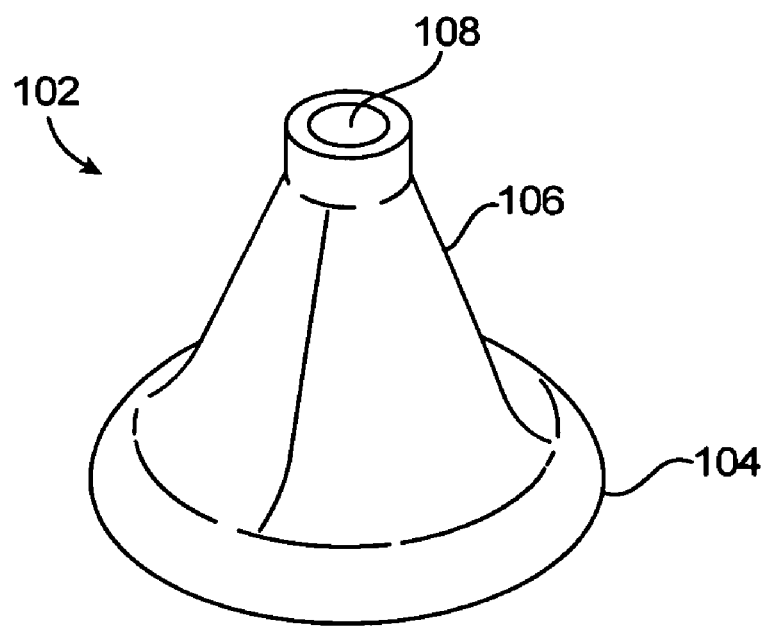
FIG. 1 shows a perspective view of an embodiment of a suction element of the invention.

FIG. 1 shows a perspective view of one example embodiment of a suction element 102 in isolation. The main body of the suction element 102 comprises a polyhedral shell 106, an elliptical o-ring like structure (hereafter o-ring 104), and a vacuum port 108. While elliptical shapes have been found to produce a good seal with the tissue surfaces, other shapes may be useable. In the embodiment seen in FIG. 1, the elliptical shape is a circle.

Figure 2:
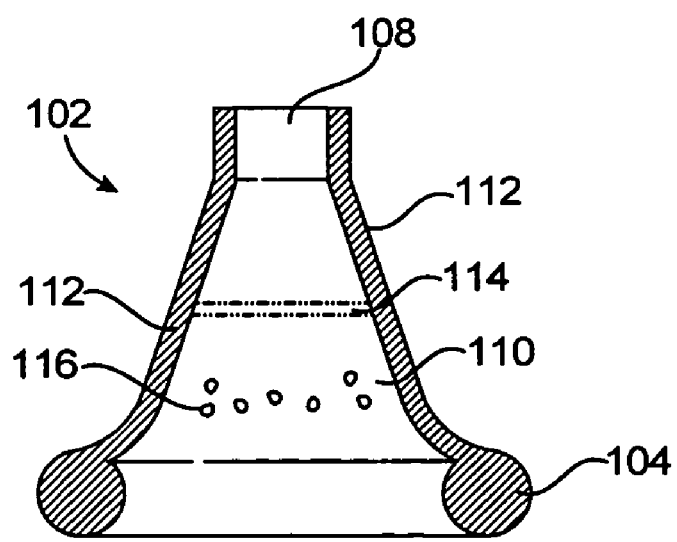
FIG. 2 shows cutaway side view of an embodiment of a suction element of the invention.

The interior cavity or chamber of the suction element 102 is preferably a polyhedral shape. In the embodiment shown in FIG. 2, the chamber 110 of the suction element 102 is defined by four roughly flat sides, creating a somewhat pyramid shape. The acute angles and flat faces of the pyramid shape above the o-ring 104 have been found to enhance the grip of the positioners of the invention because tissue drawn into the chamber 110 of the suction element 102 through the o-ring 104 cannot fully conform to the shape of the chamber 110, thereby facilitating the communication of vacuum along the walls 112 of the chamber 110 of the suction element 102 to a greater surface area of the tissue.

Other shapes including angles, but especially acute angles, and flat faces may provide a similar benefit when combined with an elliptical o-ring for contacting the tissue or organ to be positioned. Therefore, for example, in alternate embodiments, three walls may be used, and in still other embodiments, more than four walls may be used.

In some embodiments, the suction element 102 may include a screen, mesh or other pneumatically permeable membrane 114 positioned within the chamber 110 to divide the chamber 110 into two and to prevent material from clogging the vacuum port 108, or to act as a ceiling limiting the extent to which tissue may be drawn into the chamber 110. In some embodiments, the internal surfaces of the suction element 102 may also include optional texture 116 to aid in gripping tissue that has been drawn into the suction element 102 under vacuum. The texturing may include rows of dimples or bumps, or other designs that reduce movement relative to the tissue surface. Alternatively, the surface of the walls 112 may be modified by placing a physiologically-acceptable adhesive thereon to assist in adhering to the tissue to be positioned or stabilized.

In general, the suction element 102 is configured so that as vacuum is applied through the vacuum port 108, gas is evacuated from the chamber 110 applying negative pressure to a large region of tissue. Specifically, tissue does not easily conform to the polyhedral shape of the internal walls of the membrane and negative pressure is therefore not applied only to the tip of the tissue within the chamber 110, as is the case with some prior art suction devices having, for example, a cylindrical or cone shaped chamber.

Figure 3:
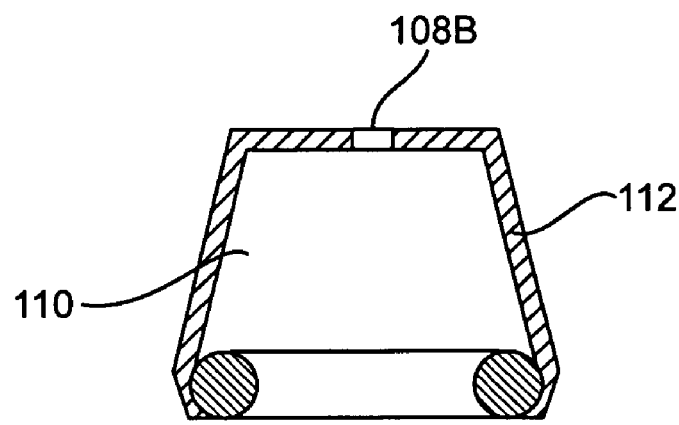
FIG. 3 shows cutaway side view of a second embodiment of a suction element of the invention.

A second example embodiment of the suction element 102 is seen in FIG. 3, which shows the o-ring 104 formed inside the polyhedral walls at the opening of the chamber 110. This embodiment allows tissue to be drawn into the suction element above the midline of the o-ring 104 under application of negative pressure and may create a mechanical advantage by allowing the tissue to conform behind the protrusion of the o-ring 104 within the suction element 102, creating contact forces between the tissue and the o-ring 104 that oppose motion of tissue out of the suction element 102.

The combination of the action of the o-ring 104 with the polyhedral shape of the chamber 110 body of the suction element 102 has been found to greatly improve vacuum adhesion, and in many cases allows tissue positioners built in accord with the invention to remain attached without active vacuum.

The suction element 102 may be fabricated from a variety of acceptable medical grade materials. In some embodiments intended for use on the heart, the preferred characteristics of the material chosen include a flexible polymeric material suitable for contacting tissue that facilitates elastic deflection of the attachment with the beating of the heart, allowing more normal function of the heart. In some embodiments, the selected material and geometry may dampen the motion of the heart with an inherent spring-like resistance of the material and optimize the performance of the positioner by allowing the force of the heart to elastically distort the material of the body of the suction element 102 rather than act to work against the seal of the suction element 102 when the force of the beating heart acts to withdraw tissue from the suction element 102. In other embodiments the flexibility of the suction element 102 may allow the suction element 102 to flex when attached to a beating heart to reduce impairment of heart function caused by using the suction element 102 to position the heart. Suitable materials for manufacturing the suction element 102 may include silicones, polyurethanes, polypropylene, polyethylene, and the like. Sources for the material include those commercially available from sources such as Dow, Bayer, UG and many others. Silicone is preferred in some embodiments, particularly silicone with a durometer rating of about 50–100 Shore.

The suction elements 102 of the invention may be constructed in any practical size and can be easily adapted by one skilled in the art as necessary for any particular purpose. In some embodiments, the suction elements 102 are small enough to be introduced through 5–30 mm port, cannula, or other opening for use in minimally invasive procedures. It is also possible to provide the device as a family of products which are geometrically configured or sized and specifically optimized for the tissue or region targeted for stabilization.

In some embodiments, improved function has been obtained by fabricating suction elements having a 1:4 ratio of the area of the vacuum port 108 to the area of the opening of the chamber 110 of the suction element 102 that contacts tissue.

Positioners built in accord with the invention may have a variety of configurations, and several example configurations will be discussed below in relation to the figures. The positioners each include at least one suction element 102 fabricated in accord with the invention. In some embodiments the suction elements 102 may be permanently coupled to the positioner 100. In other embodiments, the suction elements 102 may be disposable and replaceable.

Figure 4:
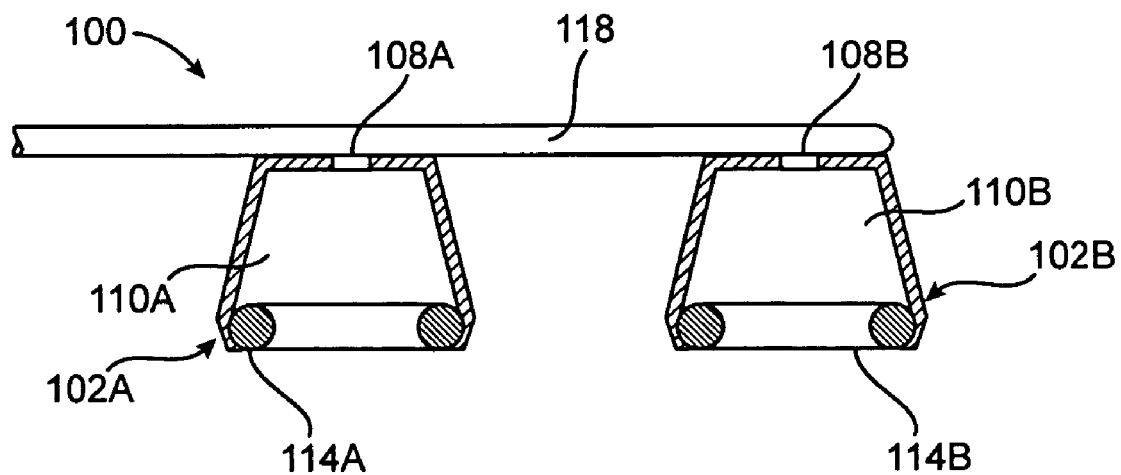
FIG. 4 shows a cutaway side view of an example embodiment of the positioner with two suction elements.

FIG. 4 shows a cutaway side view of an example positioner 100 built in accord with the invention having two suction elements 102A and B connected by a tubular structure 118 for holding the suction elements 102A and B in a selected relative position and for providing vacuum to the suction elements 102. Obviously, in alternate embodiments only one suction element 102 may be used, or more than two suction elements 102 may be used. In the embodiment of FIG. 4, the tube 118 is coupled to the top of suction element 102A and suction element 102B. In alternate embodiments virtually any desired means for providing vacuum to both suction elements 102A and B may be used, and other means for providing vacuum to each suction element 102A and B are well known in the art. The location, shape, and size of the vacuum ports 108A and B may be easily varied by one skilled in the art depending on the configuration and the intended use of the positioner 100.

In some embodiments the vacuum tubing 118 is formed of a malleable material such as medical grade stainless steel that may be bent by the user to position the suction elements 102A and B in a selected orientation and position relative to each other and to the tissue to be positioned. However, in other embodiments many kinds of commercially available tubing may be useable, including various medical grade metals, rubbers, plastics, and combinations thereof.

Figure 5:
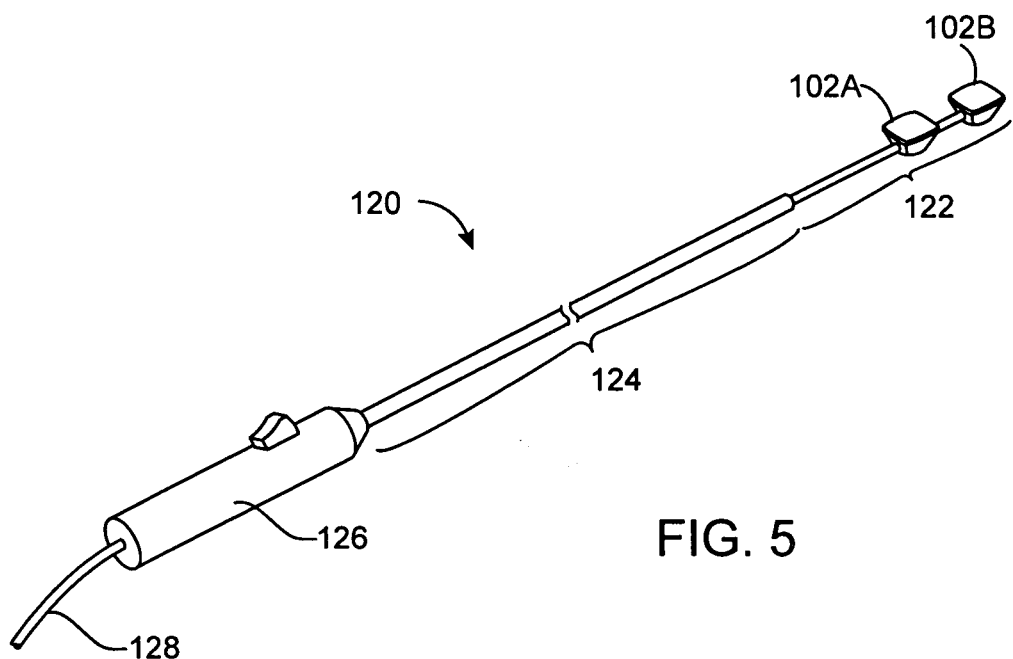
FIG. 5 shows a positioner embodiment including a steerable catheter.
Figure 6:
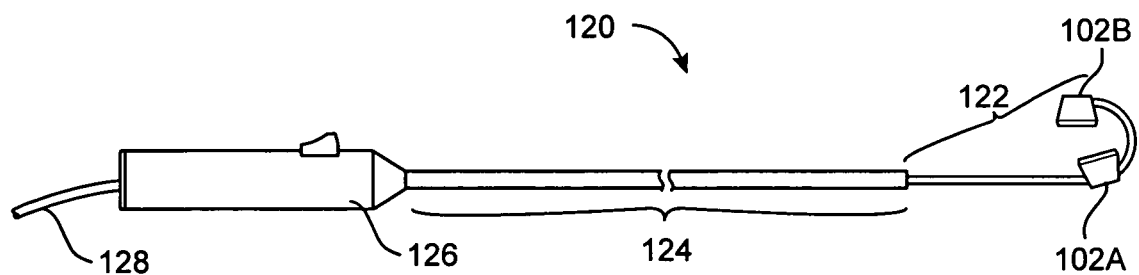
FIG. 6 shows the steerable catheter of FIG. 6 with the steerable portion of the catheter turned.

In some embodiments, the tissue positioner 100 includes a guide wire or a steerable catheter. FIG. 5 shows an embodiment of the invention wherein the positioner is a steerable catheter 120 with multiple (2 shown) suction elements 102A and B mounted to the steerable portion 122 of the catheter 120 and separated by specific lengths along the steerable portion 122 of the catheter 120. Clearly, in alternate embodiments only one suction element 102 may be used, or more than two suction elements 102 may be used. In the embodiment seen in FIG. 5, the positioner 100 includes an inflexible section 124 between a handle 126 and the steerable section 208 of the catheter. In some embodiments, the steerable catheter 120 may be capable of motion with at least one degree of freedom, and may be able to form a semi-elliptical turn with a minimum radius as small as 1 cm. This allows the suction elements 102 to be introduced through a small incision or port or trocar, and to then be steered into position before adhering to selected tissues. FIG. 6 shows the flexible portion 208 of the catheter deflected into a U-shaped turn. The steerable catheter should also have sufficient rigidity to enhance the ability of the user to manipulate the tissue to which the tissue positioner 100 is adhered by. In some embodiments for endoscopic use the total height and width of each suction element 102 is preferably less than 30 mm. In alternate embodiments, the suction elements 102 of the invention may be easily adapted for use used on a variety vacuum catheter configurations by one skilled in the art. In still other embodiments the catheter 120 may be rigid and not streerable.

Referring still to FIGS. 5 and 6, the positioner 100 may plug into the operating room vacuum system via flexible plastic tubing 128 that connects to the handle 212 of the tissue positioner 100 200. The suction is then passed through the handle 212 into and through the inflexible shaft 210 to the flexible shaft 208 and into the suction elements 102 204 and 206.

In some embodiments, once the positioner is deployed and adhered to a tissue to be positioned, it is desirable to locked it into place both rotationally and axially while maintaining stable orientation of the particular organ in question. This allows the surgeon to release the positioner from his hands to perform a surgical procedure.

FIG. 7, shows a tissue positioner 130 with locking and sealing assembly 136 consists of an inner cannula 134 and outer cannula 132 that are introduced to the body using standard minimally invasive surgical techniques. The tissue positioner 130 may interface with the outer cannula 132 at its proximal end with the locking and sealing assembly 136 consisting of a threaded cap 138, and locking knob 140 and a typical rubber o-ring 142. This locking and sealing assembly 136 is installed distal to the handle 126 of the tissue positioner 130 but proximal to the suction elements 102A and B. The shaft or vacuum tube 118 of the inner cannula can move linearly through the outer cannula 132. The outer cannula 132 is introduced to the body, the inner cannula 134 with suction elements 102A and B is introduced into the thoracic cavity through the outer cannula 132, the suction elements 102A and B are adhered to the tissue to be positioned, then the locking assembly 136 is manipulated to lock the inner cannula 134 relative to the outer cannula 132 to fix the position of the tissue to be positioned.

Another embodiment seen in FIG. 8 is as described above, except that the threaded cap 138 includes a female luer cap consists of threads to attach to the outer cannula as well as a female luer fitting that attaches to a standard hemostasis valve 146 which locks onto the inner cannula. This standard hemostasis valve may have a male luer fitting which allows detachment from the outer cannula threaded cap 138 or may be integrated with the threaded cap 138. In addition, it may be desirable in some embodiments that the locking port seal with the tissue positioner in such a way as to allow insufflation of the surgical site if desired.

FIG. 9 shows a further example embodiment of a positioner 100 built in accord with the invention that includes a single suction element 102 releasably coupled to a lockable flexible articulating arm 148, with the suction element 102 attached to a heart. Many acceptable lockable articulating arms are known in the art. The lockable flexible arm may be attached to a support structure such as a retractor 150. The vacuum tube 128 provides vacuum to the suction element 102. In alternate embodiments virtually any known means for holding a surgical device in a selected position may be used including but not limited to various arms, rods, cannula, catheters, and retractors used alone or in combination.

Figure 10:
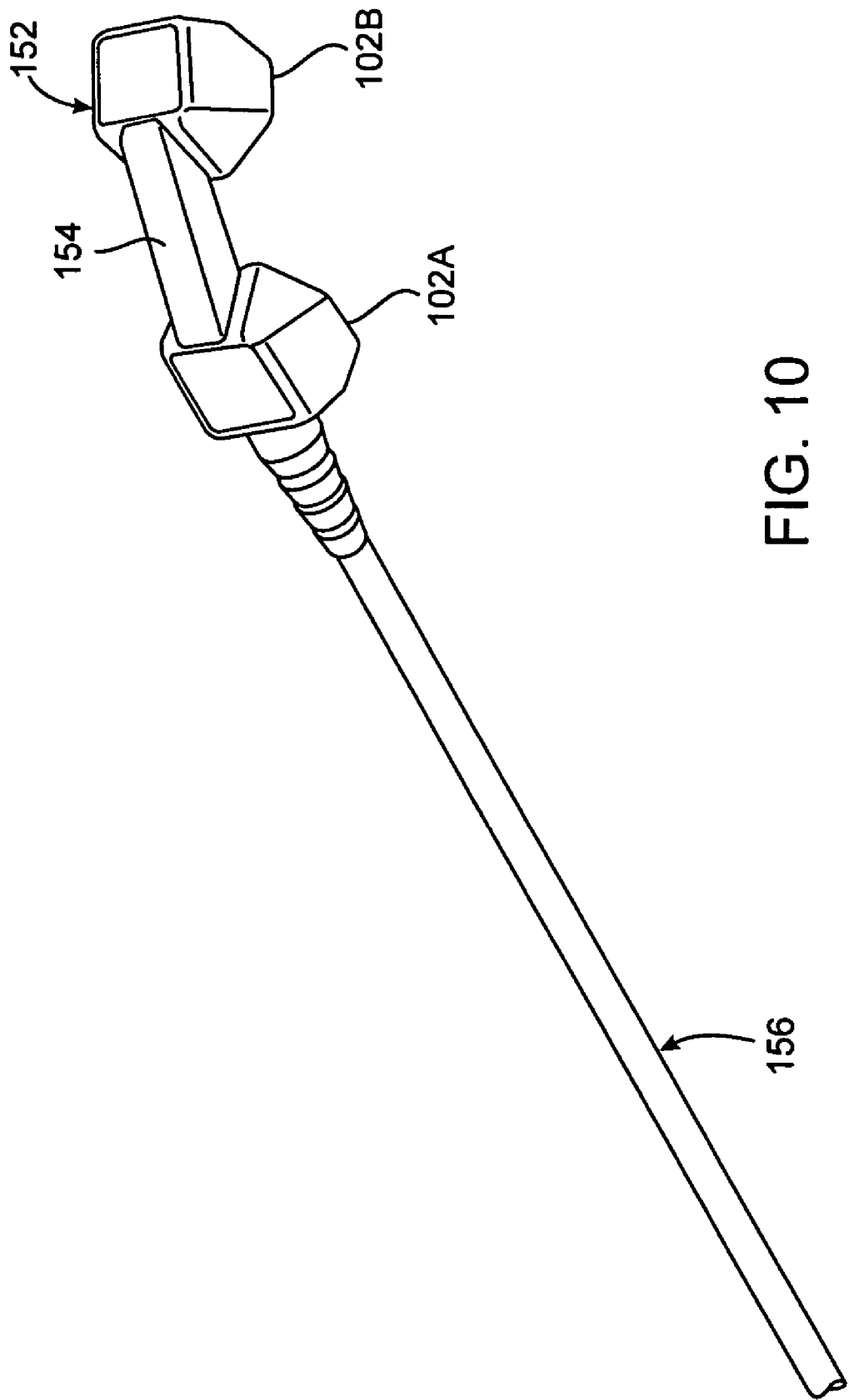
FIG. 10 shows a back perspective view of shows a positioner of the invention including two suction elements in a single suction assembly.
Figure 11:
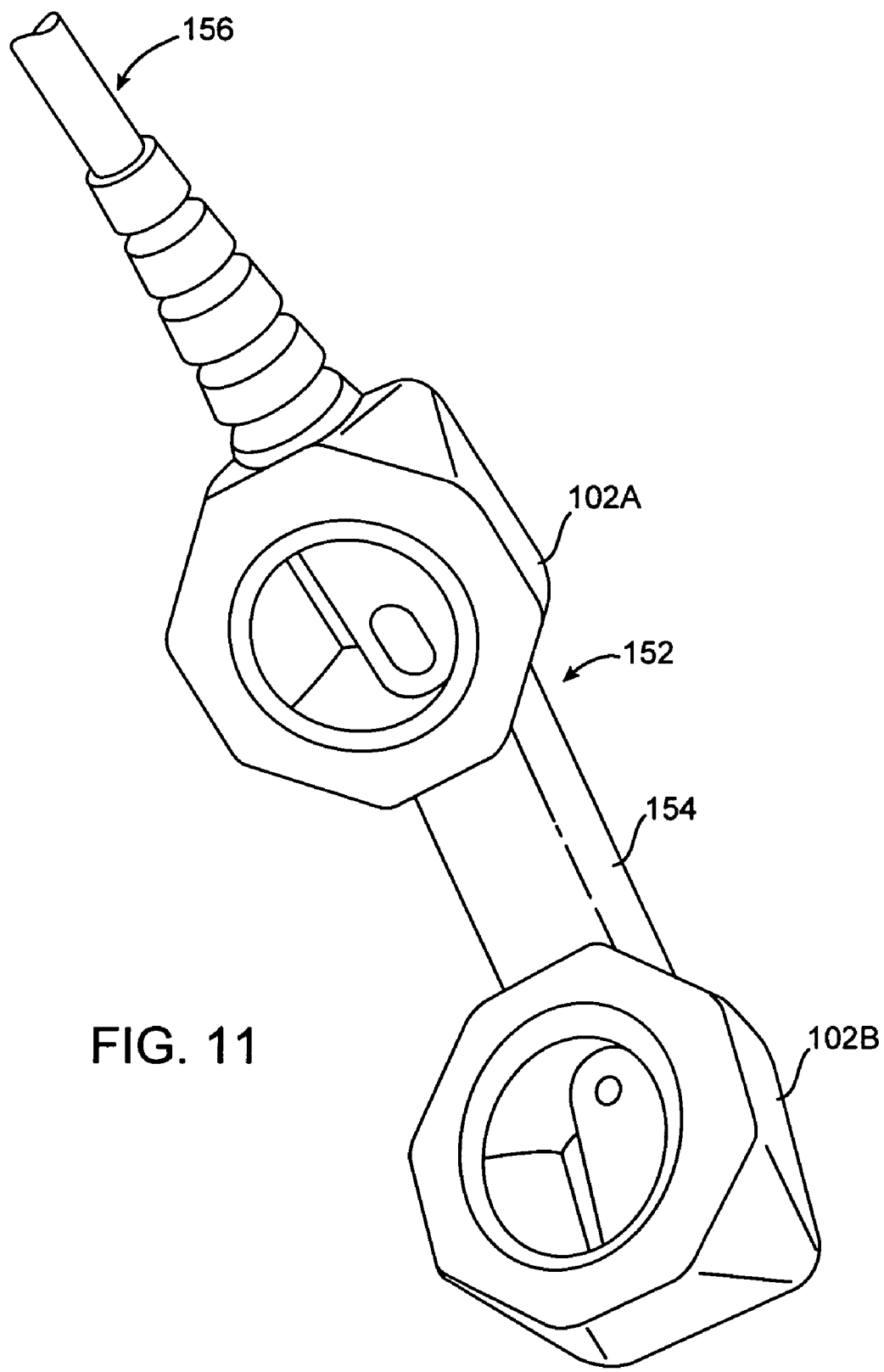
FIG. 11 shows a front perspective view of the suction assembly of FIG. 10.

FIG. 10 shows an embodiment of the invention comprising a double suction element assembly 152 comprising two suction elements 102A and 102B. In some embodiments, the two suction elements 102A and B are fixedly oriented with their bases at an angle between 5 and 180 degrees to conform to the topography of the heart. In other embodiments, the communicating suction channel 154 between the two suction elements 102A and B has a cross section selected to minimizes the potential for axial rotation between the two suction elements 102A and B. FIG. 11 shows a front view of the double suction element.

Figure 12:
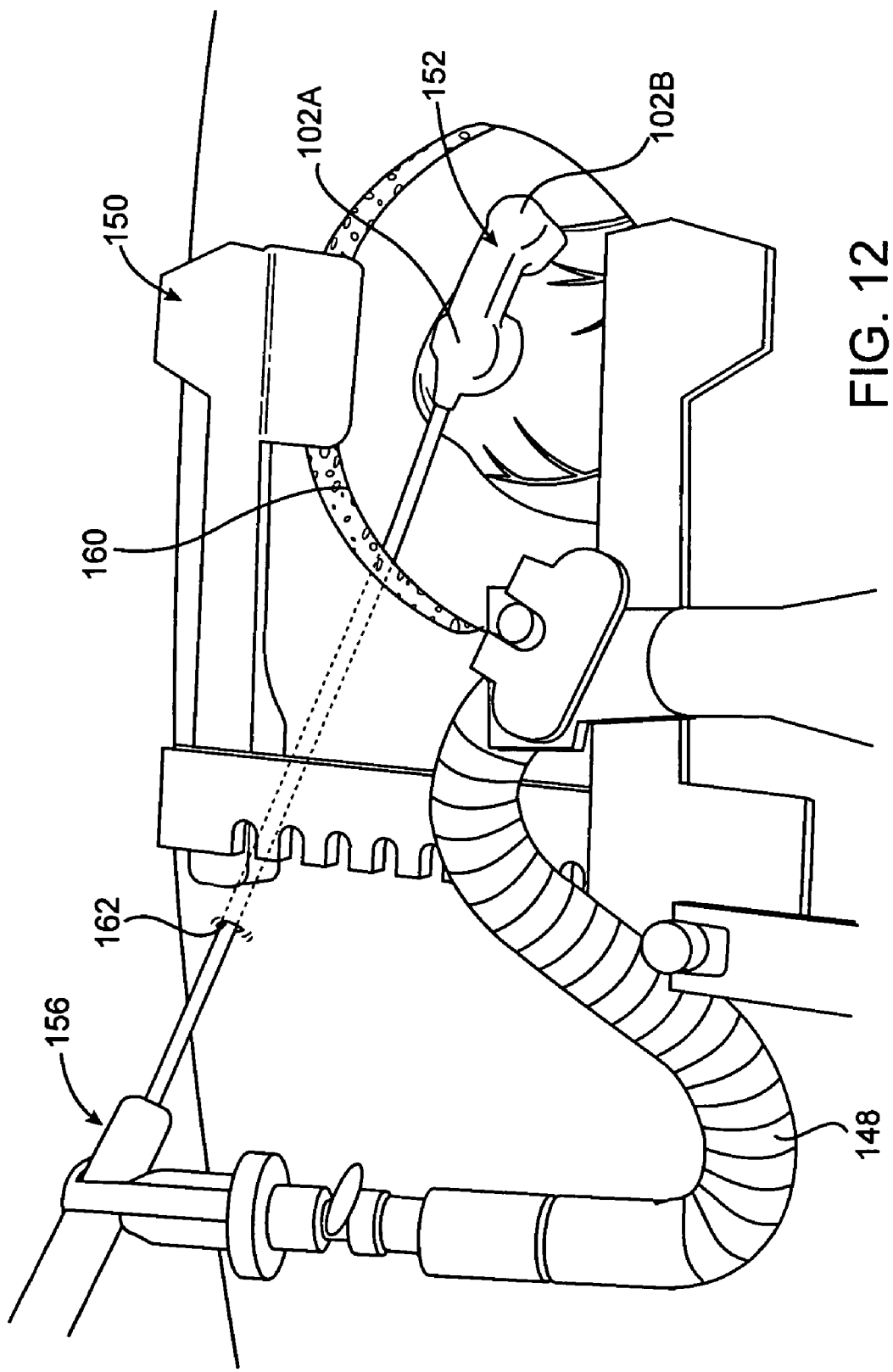
FIG. 12 shows a the suction assembly of FIG. 10 on a positioner coupled to a retractor by a flexible arm, and the suction assembly grasping tissue.

FIG. 12 shows the double suction element assembly grasping a heart. The double suction assembly 152 is supported on the end of a catheter 156 which is coupled to a retractor 150, by a flexible arm 148, to hold the catheter 150 and consequently the heart grasped by the suction elements 102A and 102B in a desired position. In open surgical procedures, the size of the opening can be reduced if some of the devices being used do not have to access the surgical field through the opening 160. FIG. 12 shows such a configuration. The shaft of the catheter has been inserted through a minimally invasive puncture 162 and the suction assembly 152 attached after insertion. The attached suction assembly 152 could also have been deployed directly through a small opening or port. However, the option to attach the suction elements after insertion of the catheter allows the use of suction elements that are larger than may easily be deployed through a small incision or port.

The invention may further include a method of manipulating, positioning and stabilizing the tissue through a minimally invasive incision in the chest by introducing an tissue positioner configured in accord with the invention through a limited access port, and attaching at least one suction member to tissue under vacuum, to facilitate remote manipulation of the distal end by contouring, pushing, pulling, or rotating the device from the proximal end to shift, move, roll, lift, press, or otherwise manipulate the tissue. In embodiments with multiple suction elements, the method of attachment may include the steps of attaching the first suction element to tissue via vacuum, then manipulating the positioner to conform to the topography of the tissue (heart for example) bringing the additional suction elements into contact with tissue. As each suction element comes into contact with tissue a seal is established automatically. Positioning by means such as the heart. In some methods, a means for holding one or more suction element of the invention, including but not limited to lockable flexible arms, retractors, catheters, vacuum tubes, rods, cannula, and fixed arms, may be introduced to a surgical field, and then one or more suction elements are affixed to said holding means through another opening in the surgical field.

The invention now being fully described, it will be apparent to one of ordinary skill in the art that many changes and modifications can be made thereto without departing from the spirit or scope of the appended claims.

Any and all publications and patent applications mentioned in this specification, or upon which priority has been claimed, are herein incorporated by reference to the same extent as if each individual publication or patent application was specifically and individually indicated to be incorporated by reference.

What is claimed is:

1. A suction element for gripping tissues comprising:
   walls defining a polyhedral shaped chamber,
   a vacuum port in gas communication with said chamber,
   an elliptical shaped ring adapted for contacting the surface of the tissues to be positioned, said elliptical shaped ring positioned at an opening of said chamber.

2. The suction element of claim 1 further comprising a screen dividing said chamber into a first and second chamber.

3. The suction element of claim 1 wherein said walls comprise at least three walls.

4. The suction element of claim 3 wherein said walls comprise at least four walls.

5. The suction element of claim 1 wherein said elliptical shaped ring is circular.

6. The suction element of claim 1 wherein said polyhedral shape includes acute angles between said walls.

7. The suction element of claim 6 wherein said polyhedral shape is roughly a pyramid shape.

8. The suction element of claim 1 wherein said walls comprise a texture on an interior surface of at least one of said walls.

9. The suction element of claim 1 wherein said elliptical shaped ring is positioned inside said chamber at said opening of chamber.

10. The suction element of claim 9 wherein said elliptical shaped ring has a midline, whereby tissue may be drawn through said elliptical shaped ring above said midline of said elliptical shaped ring to enhance a grip of said suction element on the tissues.

11. The suction element of claim 1 in combination with a vacuum source.

12. The suction element of claim 1 wherein said suction element comprises a medical grade flexible polymeric material.

13. The suction element of claim 12 wherein when said flexible polymeric material allows said suction element to flex when attached to a beating heart to reduce impairment of heart function caused by using said suction element to position said heart.

14. The suction element of claim 1 wherein a ratio of an area of said vacuum port to an area of said opening of said chamber is approximately 1:4.

15. The suction element of claim 1 in combination with a means for holding said suction element in a fixed position.

16. The suction element of claim 14 wherein said means for holding said suction element in a fixed position is selected from the group consisting of: a lockable flexible arm, a retractor, a catheter, a vacuum tube, a rod, a cannula, and a fixed arm.

17. A tissue positioner comprising
at least one suction element, said suction element including a polyhedral shaped chamber defined by at least three walls, a vacuum port in gas communication with said chamber, and an elliptical shaped ring adapted for contacting the surface of the tissues to be positioned, said elliptical shaped ring positioned at an opening to said chamber,
a conduit in gas communication with said vacuum port for providing vacuum to said chamber,
means for holding said suction element in a fixed position.

18. The tissue positioner of claim 17 wherein said suction element further comprises a screen dividing said chamber into a first and second chamber.

19. The tissue positioner of claim 17 wherein said at least three walls of said suction elements comprise four walls.

20. The tissue positioner of claim 17 wherein said elliptical shaped ring is circular.

21. The tissue positioner of claim 17 wherein said polyhedral shape includes acute angles between said walls.

22. The tissue positioner of claim 17 wherein said walls comprise a texture on an interior surface of at least one of said walls.

23. The tissue positioner of claim 17 wherein said elliptical shaped ring is positioned inside said chamber at said opening of chamber.

24. The tissue positioner of claim 23 wherein said elliptical shaped ring has a midline, whereby tissue may be drawn through said elliptical shaped ring above said midline of said elliptical shaped ring to enhance a grip of said suction element on the tissues.

25. The tissue positioner of claim 17 wherein said suction element comprises a medical grade flexible polymeric material.

26. The tissue positioner of claim 25 wherein said flexible polymeric material allows said suction element to flex when attached to a beating heart to reduce impairment of heart function caused by using said tissue positioner to position said heart.

27. The tissue positioner of claim 17 wherein a ratio of an area of said vacuum port to an area of said opening of said chamber is approximately 1:4.

28. The tissue positioner of claim 17 wherein said means for holding said suction element in a fixed position is selected from the group consisting of: a lockable flexible arm, a retractor, a catheter, a vacuum tube, a rod, a cannula, and a fixed arm.

29. The tissue positioner of claim 17 wherein said suction element is replaceable.

30. The tissue positioner of claim 17 comprising two suction elements.

31. The tissue positioner of claim 30 wherein said suction elements are attached to said positioner at a fixed distance and orientation relative to each other.

32. The tissue positioner of claim 31 wherein a portion of said positioner between said two suction elements is malleable, whereby said portion of said positioner between said two suction elements may be bent to alter said distance and orientation of said two suction elements relative to each other.

33. The tissue positioner of claim 1 wherein said at least one suction element comprises a suction assembly including two suction elements.

34. The tissue positioner of claim 33 wherein said two suction elements of said suction assembly are joined by a spacer holding said suction elements a fixed distance and orientation relative to each other.

35. The tissue positioner of claim 34 wherein each of said two suction elements comprise a central axis extending from a top of each said suction element through a bottom of each said suction element, and wherein said suction element is placed so said central axis of each suction element intersect.

36. The tissue positioner of claim 35 wherein an angle formed by said intersection of said central axes of each suction element ranges between 5 and 180 degrees.

37. The tissue positioner of claim 17 wherein said suction element is sized to pass through an opening between 5 mm and 30 mm in diameter.

38. A method for positioning tissue, which method comprises the steps:
(a) positioning a tissue positioner on the tissue to be positioned, wherein said tissue positioner comprises at least one suction element comprising:
(i) walls defining a polyhedral shape chamber,
(ii) a vacuum port in gas communication with said chamber,
(iii) an elliptical shaped ring for contacting the surface of the tissues to be positioned, said elliptical shaped ring positioned at an opening to said chamber, and
(iv) means for holding said at least one suction element in a fixed position; and
(b) attaching a negative pressure source to the vacuum port of said suction element.

39. The method of claim 38 further comprising the step (c) manipulating said suction element to move said tissue into a desired configuration and position.

40. The method of claim 39 further comprising the step (d) holding said suction element in a selected position to hold said tissue in a selected position.

41. The method of claim 38 further comprising the step (c) holding said suction element in a selected position to hold said tissue in a selected position.

42. The method of claim 39, wherein the tissue is of an internal organ.

43. The method of claim 42, wherein said internal organ is a heart.

44. The method of claim 38 wherein said suction element further comprising a screen dividing said chamber into a first and a second chamber.

45. The method of claim 38 wherein said walls of said suction element comprise at least three walls.

46. The method of claim 38 wherein said walls of said suction element comprise at least four walls.

47. The method of claim 38 wherein said elliptical shaped ring is circular.

48. The method of claim 38 wherein said polyhedral shape includes acute angles between said walls.

49. The method of claim 38 wherein said walls of said suction element comprise a texture on an interior surface of at least one of said walls.

50. The method of claim 38 wherein said elliptical shaped ring of said suction element is positioned inside said chamber at said opening of chamber.

51. The method of claim 28 wherein said elliptical shaped ring has a midline, whereby tissue may be drawn through said elliptical shaped ring above said midline of said elliptical shaped ring to enhance a grip of said suction element on the tissues.

52. The method of claim 38 wherein said suction element comprises a medical grade flexible polymeric material.

53. The method of claim 52 wherein said flexible polymeric material allows said suction element to flex when attached to a beating heart to reduce impairment of heart function caused by using said tissue positioner to position said heart.

54. The method of claim 38 wherein a ratio of an area of said vacuum port to an area of said opening of said chamber of said suction element is approximately 1:4.

55. The method of claim 38 wherein said means for holding said suction element in a fixed position is selected from the group consisting of: a lockable flexible arm, a retractor, a catheter, a vacuum tube, a rod, a cannula, and a fixed arm.

56. The method of claim 38 wherein said suction element is replaceable.

57. The method of claim 38 comprising two suction elements.

58. The method of claim 57 wherein said suction elements are attached to said positioner at a fixed distance and orientation relative to each other.

59. The method of claim 58 wherein a portion of said positioner between said two suction elements is malleable.

60. The method of claim 58 further comprising the step: bending said positioner between said two suction elements to alter said distance and orientation of said two suction elements relative to each other.

61. The method of claim 38 wherein said at least one suction element comprises a suction assembly including two suction elements.

62. The method of claim 61 wherein said two suction elements are joined by a spacer holding said suction elements a fixed distance and orientation relative to each other.

63. The method of claim 62 wherein each of said two suction elements comprise a central axis extending from a top of each said suction element through a bottom of each said suction element, and wherein said suction element is placed so said central axis of each suction element intersect.

64. The method of claim 63 wherein an angle formed by said intersection of said central axes of each suction element ranges between 5 and 180 degrees.

65. The method of claim 38 wherein said suction element is sized to pass through an opening between 5 mm and 30 mm in diameter.

66. A method for positioning tissue, which method comprises the steps:
(a) providing a positioner comprising at least one suction element comprising
(i) walls defining a polyhedral shape chamber,
(ii) a vacuum port in gas communication with said chamber,
(iii) an elliptical shaped ring for contacting the surface of the tissues to be positioned, said elliptical shaped ring positioned at an opening to said chamber, and
(iv) means for holding said at least one suction element in a fixed position; and
(b) introducing said suction elements of said positioner into a patient through a small incision or port;
(c) attaching at least one suction element to tissue under vacuum.
(d) manipulating said positioner to move said tissue into a selected position.

67. The method of claim 66 wherein said positioner comprises a first suction element and a second suction element.

68. The method of claim 67 wherein step (c) comprises the sub steps of attaching said first suction element to tissue via vacuum, then manipulating said positioner to conform to a topography of the tissue to be positioned and bringing said second suction element into contact the tissue.

69. A method for positioning tissue, which method comprises the steps:
(a) introducing a positioner into a patient through a small incision or port;
(b) Attaching at least one suction element to a portion of said positioner within the patient, said suction element comprising
(i) walls defining a polyhedral shape chamber,
(ii) a vacuum port in gas communication with said chamber,
(iii) an elliptical shaped ring for contacting the surface of the tissues to be positioned, said elliptical shaped ring positioned at an opening to said chamber, and
(iv) means for holding said at least one suction element in a fixed position; and
(c) applying vacuum to attach at least one suction element to tissue under vacuum.
(d) manipulating said move to position said tissue into a selected position.

* * * * *